United States Patent
Fetz et al.

(10) Patent No.: US 10,029,250 B2
(45) Date of Patent: Jul. 24, 2018

(54) EJECTION MECHANISM FOR PIPETTE TIPS

(71) Applicant: Integra Biosciences AG, Zizers (CH)

(72) Inventors: Adrian Fetz, Chur (CH); Noel Pasquier, Landquart (CH)

(73) Assignee: Integra Biosciences AG (CH)

( * ) Notice: Subject to any disclaimer, the term of this patent is extended or adjusted under 35 U.S.C. 154(b) by 0 days.

(21) Appl. No.: 15/402,278

(22) Filed: Jan. 10, 2017

(65) Prior Publication Data
US 2017/0197205 A1 Jul. 13, 2017

(30) Foreign Application Priority Data
Jan. 11, 2016 (CH) ........................... 0034/16

(51) Int. Cl.
B01L 3/02 (2006.01)

(52) U.S. Cl.
CPC ........... *B01L 3/0237* (2013.01); *B01L 3/0279* (2013.01); *B01L 2200/04* (2013.01); *B01L 2300/024* (2013.01); *B01L 2300/027* (2013.01)

(58) Field of Classification Search
None
See application file for complete search history.

(56) References Cited

U.S. PATENT DOCUMENTS

| | | | | |
|---|---|---|---|---|
| 4,616,514 A * | 10/1986 | Magnussen, Jr. | ..... | B01L 3/0227 403/369 |
| 2005/0118069 A1 | 6/2005 | Solotareff et al. | | |
| 2005/0155438 A1 * | 7/2005 | Belgardt | ............... | B01L 3/0217 73/864.01 |
| 2008/0286157 A1 * | 11/2008 | Mathus | ................. | B01L 3/0279 422/513 |
| 2009/0274587 A1 * | 11/2009 | Butz | ..................... | B01L 3/0217 422/400 |
| 2011/0132110 A1 * | 6/2011 | Kimura | ................. | B01L 3/0224 73/864.01 |
| 2011/0296931 A1 * | 12/2011 | Warhurst | ............. | B01L 3/0227 73/864.01 |
| 2014/0047931 A1 | 2/2014 | Mettier et al. | | |

(Continued)

OTHER PUBLICATIONS

Switzerland search report, Switzerland patent application 00034/16, dated Apr. 21, 2016.

*Primary Examiner* — Jill Alice Warden
*Assistant Examiner* — Brittany I Fisher
(74) *Attorney, Agent, or Firm* — Andrus Intellectual Property Law, LLP

(57) ABSTRACT

The invention pertains to a handheld pipette (11) with a handle (13), an interconnecting part (15) to attach a pipette tip and an ejection mechanism to remove the pipette tip from the interconnecting part (15). The ejection mechanism has a movable slider (43) relative to the interconnecting part (15) in the area of the interconnecting part (15 that is designed to slide the pipette tip from the interconnection part (15) when operating the ejection mechanism. The pipette (11) furthermore possesses a first and a second operating element (45, 47) accessible from the outside to operate the ejection mechanism, whereby the first operating element (45) is arranged in the area of the handle (13) and is operable by hand, and where the second operating element (47) is intended to be operated by an external device (71).

13 Claims, 2 Drawing Sheets

(56) References Cited

U.S. PATENT DOCUMENTS

2014/0147349 A1* 5/2014 Schmidt ............... B01L 3/0279
                                                  422/522
2014/0199216 A1* 7/2014 Moriarty .............. B01L 3/0217
                                                  422/522
2016/0303557 A1* 10/2016 LaCroix ............... B01L 3/0224

* cited by examiner

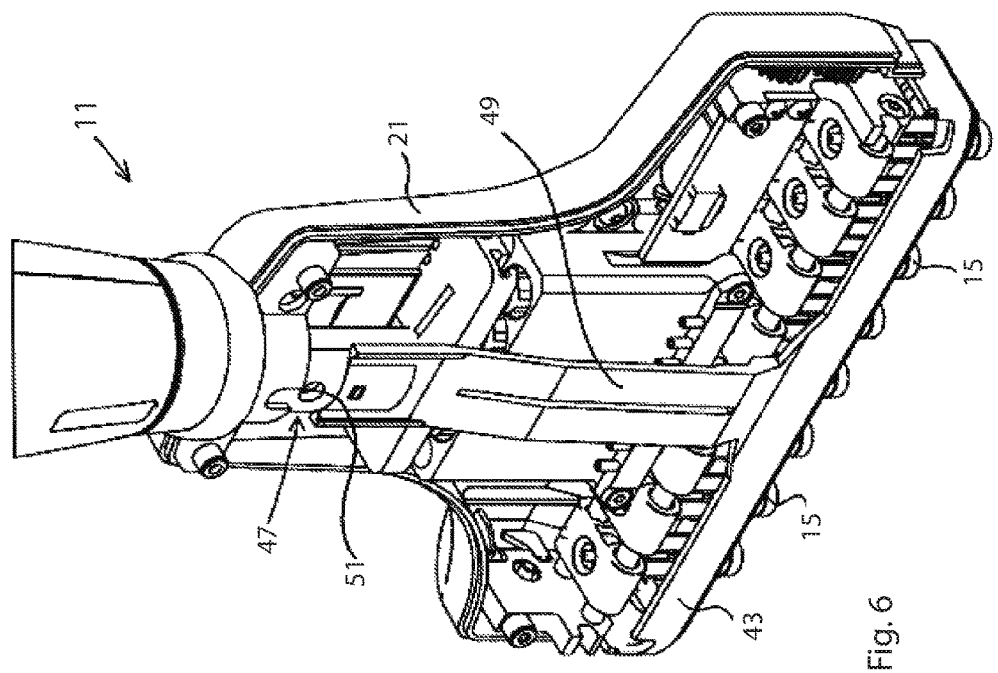
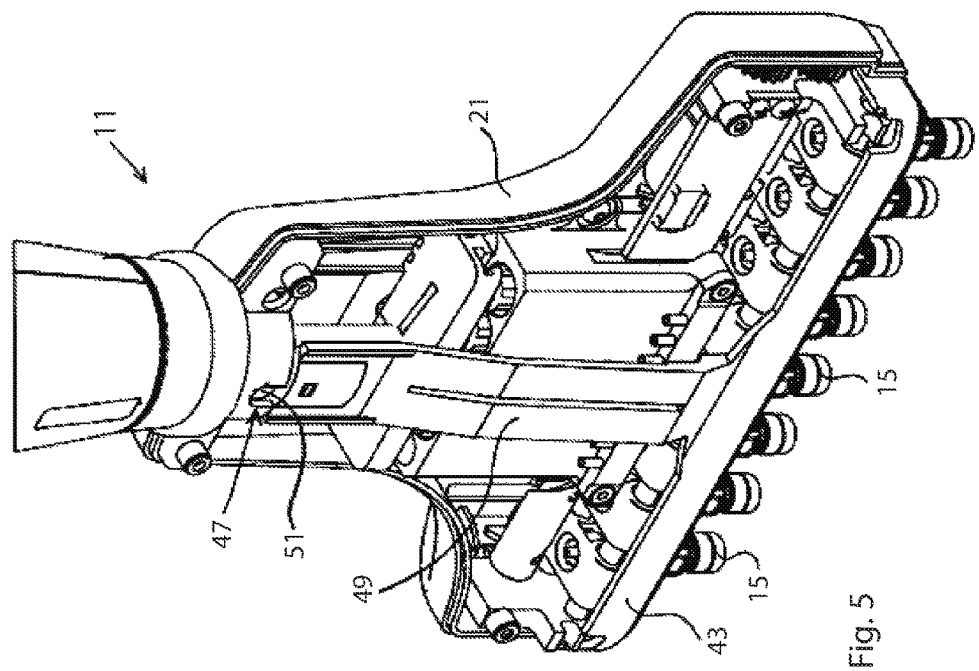

EJECTION MECHANISM FOR PIPETTE TIPS

CROSS REFERENCE TO RELATED APPLICATION

This application claims the benefit of and priority from Switzerland Patent Application No. 00034/16 filed Jan. 11, 2016 in the Switzerland Patent Office. The Swiss application is incorporated herein by reference in entirety.

FIELD OF INVENTION

The invention relates to a pipette with replaceable pipette tips comprising an ejection mechanism for the removal of pipette tips. A procedure for removing the pipette tips and a device to operate the ejection mechanism are furthermore subject matter of the invention.

BACKGROUND

Pipettes serve the dosing of liquids and are especially used in laboratories. Handheld and/or manually operational pipettes are of particular interest in connection with the invention. Such instruments comprise a sample container in which a (mostly liquid) sample to be drawn up is collected, and from which it can be dispensed again. The sample container is designed to be moved manually with the pipette, by hand in particular.

The collecting and the dispensing of a sample can be achieved, for example, by generating a negative pressure in the sample container to collect the sample, and an overpressure to dispense the sample. Piston pipettes, for example, possess a movable piston for that purpose, whereby an air column is arranged between the sample to be collected and the piston. During the movement of the piston into a first direction, the piston displaces the air column, while, during the movement into a second direction opposite a first direction, it pulls the air column and therefore also the sample to be collected into the sample container.

In order to prevent contamination, such pipettes may be provided with replaceable sample containers in the form of pipette tips. The pipette then comprises an interconnecting part that the pipette tip is pushed onto and from which it can be removed again after use. The pipette tip normally comprises two openings, whereby the interconnecting part is accommodated in the larger of the two openings during the attaching and seals it. The collecting and dispensing of the sample is done through the smaller opening. As only the pipette tip gets in contact with the sample to be collected, contamination with subsequent pipetting processes is prevented. The pipette tip is usually a disposable item made of plastic.

Besides purely mechanical pipettes, electronic pipettes also exist. Pipettes may also comprise one (with single-channel pipettes) or several (with multi-channel pipettes) interconnecting parts. Several interconnecting parts are furnished with a replaceable pipette tip to allow for the simultaneous collecting and dispensing of several samples. Depending on the quantity and attachment force used, the ejection of the pipette tips can require substantial strength. As the ejection mechanism of such pipettes is usually mechanical and operated by hand, this can result in fatigue of the hand during longer work cycles.

The ejection mechanisms used with handheld pipettes usually possess some similarities. This includes a slider that is configured to be movable along the interconnecting part. When operating the ejection mechanism, the slider is moved in the direction of the pipette tip, comes into contact with it and slides it off the interconnecting part. The ejection mechanism can be operated by means of an operating element. The operating element is usually operated by hand and is formed as a button, for example. The force exerted on the operating element can thereby be transferred to the slider mechanically and can thus effect its movement in the direction of the pipette tip. The part of the ejection mechanism that establishes the connection between the operating element and the slider can be designed in various ways, but generally comprises one or several movable links. The movement of the links is coupled with the movement of the slider. The links for the transfer of the force (when activating it) on the operating element are expediently formed on the slider.

The invention described in this document may also pertain to design variants of the previously described types of pipettes.

SUMMARY OF THE INVENTION

It is one task of the present invention to provide for a pipette with replaceable pipette tips that comprises an ejection mechanism to remove the pipette tips, and a device to activate the ejection mechanism of the pipette. By using such a device in connection with the pipette, the removal of pipette tips from the pipette can be facilitated. Further advantages of the present invention are presented in the following description.

PRESENTATION OF THE INVENTION

The above-listed task is solved through a pipette as described herein.

What is revealed, among other things, is a handheld pipette with a handle, an interconnecting part for attaching a pipette tip, and an ejection mechanism to remove the pipette tip from the interconnecting part. The ejection mechanism preferably comprises a movable slider that is formed to slide the pipette tip from the interconnecting part when activating the ejection mechanism. The pipette has a first and a second operating element to operate the ejection mechanism, whereby the first operating element may be operated by hand.

It is advantageous to use the pipette together with a device as described in this document to operate the (pipette tip) ejection mechanism of a pipette. The pipette described in this document and the device described in this document are both disclosed independently from each other and as components of one system. The joint usage and/or the interaction of the pipette and the device are furthermore disclosed for the purpose of operating the ejection mechanism.

The second operating element of the pipette is preferably not operated by hand and/or without tools, and the second operating element is designed to be operated mechanically (especially through the device described in this document) from outside.

The device may comprise a movable part that is designed to operate the second operating element and/or to interact with the second operating element to operate the ejection mechanism.

The movable part and the second operating element may advantageously be designed to engage with each other and/or to interact positive-locking. Alternatively, or additionally, the movable part and the second operating element may be formed complementary to each other. The movable part may be an extension, for example, and the operating element may comprise an opening to accommodate the extension.

A movement of the movable part relative to the device expediently effects a movement of the second operating element relative to the pipette, thus operating the second operating element and/or the ejection mechanism.

Features are described in the following, whereas these are to be considered preferred features (individually), even if they are not explicitly described as such. The features are revealed separately (as part of any pipette, any device, or any procedure) and—so far as that they don't exclude each other—in any combination thereof. This includes the possibility of the simultaneous realization of all these features.

The pipette is a handheld pipette. It can be designed to be held (with one single hand, in particular) and/or operated and/or raised during the intended use. The intended use may comprise the collecting and/or dispensing of fluid (especially liquid) samples and/or their transport by means of the pipette from a first container (source container) to a second container (target container). The pipette may especially be designed be moved from a first container to a second container entirely with one hand for the purpose of transporting a fluid sample.

The pipette comprises a handle that is advantageously formed to be held by one hand.

Advantageously the pipette weighs less than 2, 1, 0.5 or 0.3 kilograms and/or more than 10, 30, or 50 grams.

The pipette may have a device for creating a negative pressure (therefore a pressure that is lower than the atmospheric pressure) and/or an overpressure (therefore a pressure that is higher than the atmospheric pressure) in the pipette tip. By creating a negative pressure, a sample can be sucked into the pipette tip, while a sample can be ejected from the pipette tip when generating an overpressure.

Advantageously, the pipette comprises a displacement device for the displacement of a gas cushion. The displacement device comprises a moving device that can have one or several pistons. The piston is intended to expand an air cushion (when sucking in a sample into the pipette tip) and/or to compress it (when ejecting a sample from the pipette tip).

Provision may be made for that the pipette is an air displacement pipette or a direct displacement pipette.

It is advantageous if the pipette is an electronic pipette. The pipette can especially have an electronic memory.

The pipette is preferably an electronic pipette, whereby the pipette comprises a memory, whereby the memory contains information to control a device for operating an ejection mechanism. It is expedient in this case, if the pipette additionally comprises a communication device for the (preferably wireless) transmission of information to the device. The information may be entered into the memory by means of a user interface, for example. The user interface may be part of the pipette and may include a display and/or an input device (preferably with input elements such as buttons or a touchscreen), for example.

The pipette comprises one or several (e.g. at least 4 or 8 and/or at most 32 or 24) interconnecting parts. The interconnecting part may be formed conical, for example.

Advantageously, the pipette is a multi-channel pipette, which has several interconnecting parts for attaching one pipette tip each.

This pipette may be designed to dose liquid volumes of at least 0.05 or 0.1 µl and/or at most 1,000 or 5,000 or 10,000 µl per interconnecting part and/or per pipette tip.

If several interconnecting parts are present, then they are preferably arranged next to each other, and/or in a straight line and/or in parallel to each other. The interconnecting parts are formed to be connected with one pipette tip each. The pipette tips are thereby attached on the interconnecting part.

When an interconnecting part is discussed in this document, the discussion also applies alternatively to several interconnecting parts (and vice versa). The same applies to the mention of a pipette tip.

The pipette tip is exchangeable and/or can be connected with the interconnecting part detachably and/or the interconnection part is formed to repeatedly be connected with a pipette tip and to be removed from such again.

The pipette tip can be made of plastic. The pipette tip advantageously has two openings of which one is bigger than the other. The larger opening is formed to accommodate the free end of the interconnecting part and/or to interact with the interconnecting part in a clamping manner, while the smaller opening is formed for the collecting and/or disposing of a fluid, particularly liquid sample.

The connection direction is to be understood as the direction in which the pipette tip is moved in relation to the interconnection part for the purpose of the connection with the interconnecting part. The ejection direction is to be understood as the direction, in which the pipette tip is moved in relation to the interconnecting part for the purpose of removal from the interconnecting part. The connection direction and the ejection direction are advantageously arranged contrary to one another and/or are arranged along (especially substantially in parallel to) the longitudinal axis of the pipette tip and/or the longitudinal axis of the interconnecting part.

In order to connect the pipette tip with the interconnecting part, the pipette tip can be moved in the connection direction towards the interconnecting part, until the connection between the pipette tip and the interconnecting part (e.g. through clamping and/or frictional connection) has been established. To remove the pipette tip, the pipette tip can be moved in the ejection direction (particularly by means of the ejection mechanism and/or the slider), until the connection between the pipette tip and the interconnecting part has been disengaged.

The ejection mechanism has a movable slider that is relative to the pipette, particularly relative to the interconnecting part (preferably along the interconnecting part and/or towards the ejection direction). The slider is expediently formed to slide the pipette tip from the interconnecting part when operating the ejection mechanism with the pipette tip while in contact and/or getting into contact.

For example, the pipette tip may comprise an opening (the larger opening described above), whereby the opening is formed to accommodate the interconnecting part. In a simple execution, the inside adjacent to the opening can thereby interact with the outside of the interconnecting part in a clamping manner, and can form a friction-type connection. The slider may expediently get into and/or be in contact with the pipette tip in the area of the aforesaid opening; the slider may particularly get into and/or be in contact with the edge of the aforesaid opening, to slide the pipette tip away from the interconnecting part.

In a starting position and/or before operating the ejection mechanism, the slider may be arranged at a short distance (e.g. at a distance of less than 10, 5, or 3 millimeters) from the pipette tip connected with the interconnecting part. When operating the ejection mechanism, the slider moves towards the pipette tip and gets into contact with it, whereby pressure is preferably exerted on the pipette tip, which overcomes the described clamping and/or the described frictional connection.

The slider is assigned to the interconnecting part. In case there are several interconnecting parts, the slider can be assigned to several or all interconnecting parts. Accordingly, the slider (as described for a connection section) can be movable relative to the interconnection parts assigned to it and/or can slide the pipette tips (simultaneously or one after the other) from the interconnecting parts assigned to it.

The pipette has a first and a second operating element to operate the ejection mechanism. The operating elements are expediently accessible from the outside and/or operational from the outside, especially from the outside of the pipette.

The first operating element can be operated by hand. It can be a mechanical operating element such as a pushbutton or a switch, for example. It may however also be an electronic operating element such as a touchscreen, for example.

It is advantageous if in the condition, during which the pipette is held by one hand, that the first operating element can be reached and/or operated by the same hand, especially by a finger of that hand. In the condition of the pipette held in the hand, the second operating element is preferably not operational and/or not reachable by the same hand as the first operating element and/or can't be reached by the hand in question.

It is especially preferred if the second operating element is formed to interact with an external device, meaning a device that is not part of the pipette, to operate the ejection mechanism.

Preferably, the ejection mechanism can alternately be operated through the first or the second operating element and/or the operation of one of the operating elements is adequate to operate the ejection mechanism.

The ejection mechanism can be formed to transmit a force (preferably mechanical) to the slider. The ejection mechanism may especially be formed to transmit a force (preferably mechanical) exerted to the first and/or second operating element to the slider.

For instance, the ejection mechanism may comprise a movable member for this purpose. Provision may be made for the movable member to be configured to be movable relative to the interconnecting part (preferably in the same direction as the slider and/or translational and/or linear). The movable member is expediently coupled with the slider so that the movement of the member effects the movement of the slider. According to one variant, the movable member may be arranged inside the housing of the pipette.

The second operating element is advantageously arranged on the movable member and/or an operation of the first and/or second operating element effects the movement of the movable member.

The first operating element and/or the second operating element can be mechanically coupled with each other and/or with the slider and/or can connected through one or several movable members. One of the members is preferably the previously described movable member. The movable member and/or the movable members transmits force onto the slider.

It is advantageous for the movable member to be spring-loaded so that after the movement effected through the operation of the first and/or second operating element from an initial position into an end position, it is moved back again from the end position into the initial position by means of the spring force.

The second operating element is formed to interact with a device to operate the ejection mechanism. The second operating element is especially formed to interact with a mobile part of the device to operate the ejection mechanism. Preferably, the second operating element can comprise a connection means for the (for example, positive or frictional) connecting with the movable part for this purpose.

The movable part is expediently movable in the same direction as the second operating element and/or in the ejection direction.

So that the movable part of the device can interact with the second operating element for the purpose of operating the second operating element, the movable part and the second operating element can be formed correspondingly, especially complementary. For example, the movable part may comprise the shape of a pin, which can be placed in an opening of the second operating element. In general, the movable part should be configured to come into contact with the second operating element, exert a force on it and operate and/or move as described above.

The pipette may comprise a housing encompassing the ejection mechanism (and/or the movable member described above), and the second operating element may then be accessible from the outside through an opening in the housing, whereby the opening is preferably closable through a movable closure arranged on the housing. The closure may be a flap or a slider, for example. According to one variant, the closure may be rotatable or moveable linearly. Advantageously, the closure is configured to be movable along or in parallel to the surface of the housing. The external device to operate the ejection mechanism may be designed to open the closure.

According to one preferred variant, the pipette comprises a top part and a bottom part that is detachably (e.g. by means of a bayonet joint, slewing bearing, or snap connection) connected to it. The handle and the first operating element are thereby arranged on the top part. The second operating element may also be arranged on the top part. It is however preferred that the second operating element be arranged on the bottom part. The interconnecting part and the slider are arranged on the bottom part, whereby this can optionally also apply to the air displacement device or the set-up necessary to create negative pressure and overpressure (see description above), such as a piston, for example.

The external device advantageously comprises a drive (for example, an actuator or an electric motor or a piezo element), whereby the drive is designed to operate the second operating element of the pipette. The movable part of the device described above can especially be movable by means of the drive for this purpose.

According to a preferred variant, the device comprises a holder to hold the pipette, whereby the drive and/or the movable part is positioned relative to the holder and the second operating element can be operated by the drive when the pipette is held in the holder.

The external device is preferably designed to receive information from the pipette and depending on this information, to operate the second operating element, whereby the device has a communication device for this purpose for the (preferably wireless) reception of information and a microprocessor to process the information and to control the drive.

The external device is advantageously a positioning device, particularly a positioning device as described in the European Patent Application No. 2698202 A2 and corresponding U.S. Pat. No. 9,321,048. The content of the European patent application and the corresponding U.S. Pat.

No. 9,321,048 are hereby incorporated in this application in their entirety by reference; respectively such disclosure shall be considered part of the disclosure of the present application.

Advantageously, the external device is a positioning device to position the pipette when collecting and/or dispensing of samples and/or during the transport of samples from a first container to a second container. In addition to the first holder, the device then expediently comprises a second holder to hold the first or second container and a second (and operationally one or several more) drive(s) (such as an actuator or an electric motor or a piezo element, for example) to move the first holder relative to the second holder. It is additionally advantageous, if the device is designed to perform the positioning of the pipette depending on the information, and/or to perform the movement of the first holder relative to the second holder.

The second drive may be designed for the positioning of the pipette and/or its movements in possibly several directions across a work surface and/or in a direction across the work surface and/or on the work surface towards and/or away from the work surface.

A procedure to remove a pipette tip from an interconnecting part of a handheld pipette (preferably a pipette of the kind described in this document) is also disclosed. The pipette expediently comprises a handle, an ejection mechanism to remove the pipette tip from the interconnecting part as well as a first and a second operating element to operate the ejection mechanism, whereby the first operating element is arranged in the area of the handle and can be operated by hand. During the procedure, the pipette is brought into contact with a device (preferably of the type described in this document), whereby the second operating element is brought into contact (and is engaged) with a movable part of the device and is then operated through movement of the movable part.

Provision may be made for the device to have a holder and for the pipette to be held in the holder, whereby when the movable part of the device is in the connected state, when the pipette is held in the holder, it is in contact with the second operating element.

The pipette can be an electronic pipette with a memory, whereby the memory receives information to control the device, whereby the pipette and the device comprise a communication device each and the information from the pipette is transmitted to the device (preferably wirelessly). The device has a drive to move the movable part, whereby the drive is controlled in dependence of the information and the movable part is moved.

The terms in this document should preferably be understood how a specialist in the field would understand it. If several interpretations are possible in the respective context, then each interpretation shall preferably be disclosed individually. Especially in the event that there were ambiguities, the preferred definitions listed in this document may be used alternately or supplementary.

In this document, both during the use of the definite article (e.g. "the") and during the use of the indefinite article (e.g. "a") in connection with an object (unless otherwise stated), the object should be disclosed without specification, whether it deals with the same object of the same description, which is mentioned elsewhere in the document. Notwithstanding the above, it shall be disclosed that it preferably deals with the same object when mentioning an object with the same description. Examples for such objects are the housing and the movable member. When there is talk about a "device" in this document, the device is meant to operate the ejection mechanism of a pipette according to a preferred version. The "ejection mechanism" is meant to be the ejection mechanism to remove the pipette tip from the pipette according to a preferred version.

Actions that are disclosed in the form of aptitudes, abilities, characteristics, or functions of the devices (or their parts) described in this document are also revealed as process steps of the procedures (independently and in any combination), and that namely dependent and independent on the respective device or the respective device part.

The use of characteristics of the described devices or device parts (independent and in any combination) are additionally revealed as process steps of the procedure.

Conversely, the disclosed devices or device parts may comprise means that may perform one or several process steps listed in combination with the disclosed procedure and/or are designed for it.

The subsequent patent claims are additionally also revealed with a back reference to any of the previous patent claims ("according to one of the previous claims"), even if they are not claimed in this form.

BRIEF DESCRIPTION OF THE DRAWINGS

The following is shown:

FIG. 5 the bottom part of the pipette from FIG. 1 with the housing partially removed to show the second operating element in initial position; and FIG. 6 the bottom part of the pipette from FIG. 1 with the housing partially removed to show the second operating element in end position.

DETAILED DESCRIPTION

Figure 1:
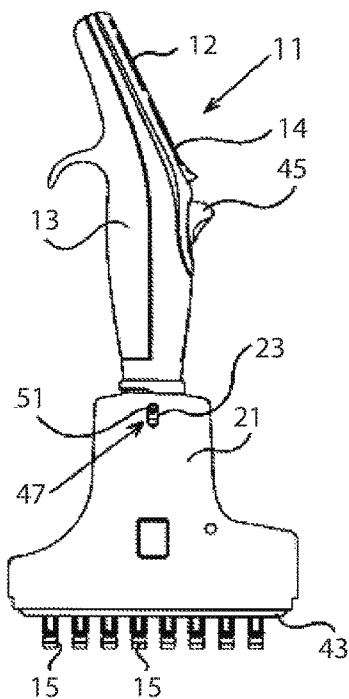
FIG. 1 a side view of a multi-channel pipette with an ejection mechanism and two operating elements.

The invention is explained below by way of example using the drawings.

All the drawings show the same pipette 11, an electronic multi-channel pipette with an ejection mechanism to remove pipette tips, whereby in FIGS. 5 and 6 only the lower part (bottom part) of the pipette 11 is represented and the housing 21 of the pipette 1 is partially removed for better illustration of the ejection mechanism. The description of device 71 to operate the ejection mechanism is described in reference to FIGS. 2, 3, and 4.

The pipette 11, a piston pipette, for instance, is designed to be held by one hand and to be used with the same hand. During use, which comprises the collecting, the transporting, and the dispensing of liquid samples, the pipette may be held and/or moved with one hand at a distance from a contact surface.

It is expedient in this connection, if a top part and/or one end of the pipette 11 is essentially formed rod-shaped so that it may be grabbed and held by one hand. A display 12 and different input elements such as buttons 14 are arranged in the area of the handle 13. An operating element 45 that can be manually operated is also located in the area of the handle 13, which may be used to operate the ejection mechanism.

The pipette 11 comprises several interconnecting parts 15 (only partially marked), on which a pipette tip (not shown)

can usually be attached. Suitable pipette tips are essentially tubular, with a larger opening on one end and a smaller opening on the opposing, usually tapered end. The larger opening essentially has the same diameter as an interconnecting part 15 and is intended to accommodate the interconnecting part 15. The smaller one of the opening serves the collecting and dispensing of the sample. When attaching the pipette tip, the interconnecting part 15 (partly) is inserted into the bigger of the two openings, whereby the outside of the interconnecting part 15 interacts with the inside of the pipette tip in a sealing manner. The pipette tip is a replaceable sample container and serves the collecting and dispensing of liquid samples, whereby the collecting is achieved by creating a negative pressure and the dispensing by creating an overpressure in the pipette tip. The interconnecting parts 15 comprise openings for the gas exchange between pipette 11 and pipette tips for this purpose.

The pipette tips are connected detachably with the interconnecting parts 15. To remove the pipette tips from the interconnecting parts 15, the pipette 11 has an ejection mechanism, which may be triggered by operation of operating elements 45 or 47. A slider 43 is intended as part of the ejection mechanism, which surrounds the interconnecting parts wholly or partially, and which is moved from an initial position to an end position and preferably back again when operating the ejection mechanism. The slider 43 thereby moves along the interconnecting parts 15, comes into contact with the pipette tips in the area of the edge of their large opening and slides the pipette tips from the interconnecting parts. Like in the present case, the slider 43 can be designed like a strip with several openings, for example, whereby the interconnecting parts 15 are arranged in the openings. Except for the slider 43 and the operating elements 45 and 47, all parts of the ejection mechanism are surrounded by the housing 21 of the pipette 11. This however represents just one possible variant.

The slider 43 is mechanically coupled with the operating elements 45 and 47, so that a movement from the first operating element 45 and/or the second operating element 47 causes the movement of the slider 43 described above along the interconnecting parts 15. The mechanical coupling may be established through one or several (relative to the interconnecting parts) movable members 49 that connect the slider 43 with the first and/or second operating elements 45, 47. As the members 49 in the present example are surrounded by the housing 21, only the member 49 connecting the slider 43 with the second operating element 47 is recognizable in FIGS. 5 and 6, in which part of the housing is removed. The first operating element 45 can be operated with one finger of the hand holding the pipette 11. The second operating element 47 however is intended to be operated by an external device 71.

Figure 2:
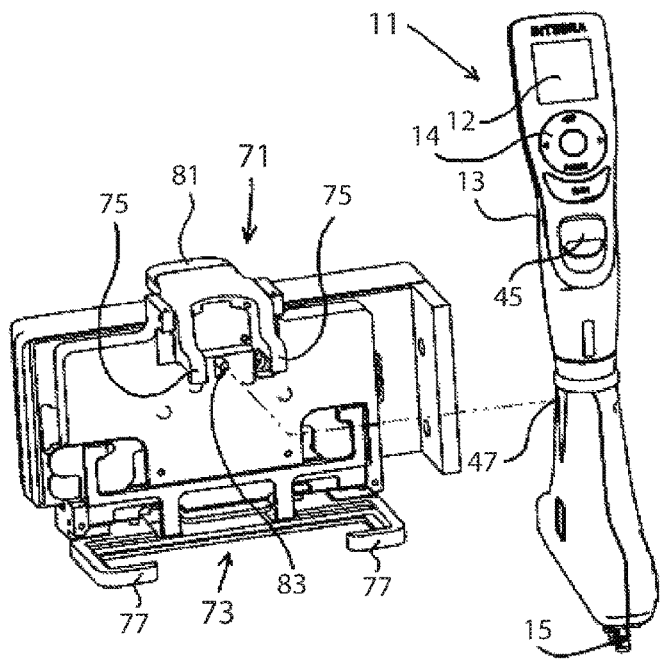
FIG. 2 a perspective view of the pipette from FIG. 1 with a device to operate the ejection mechanism.
Figure 3:
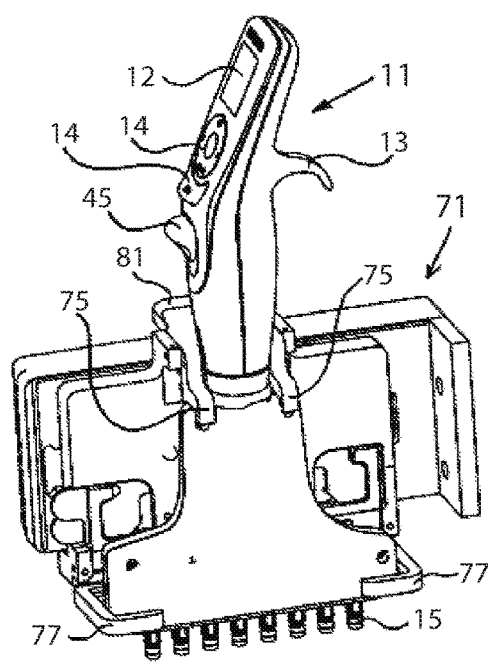
FIG. 3 a perspective view of the pipette and the device from FIG. 2 in a connected state.
Figure 4:
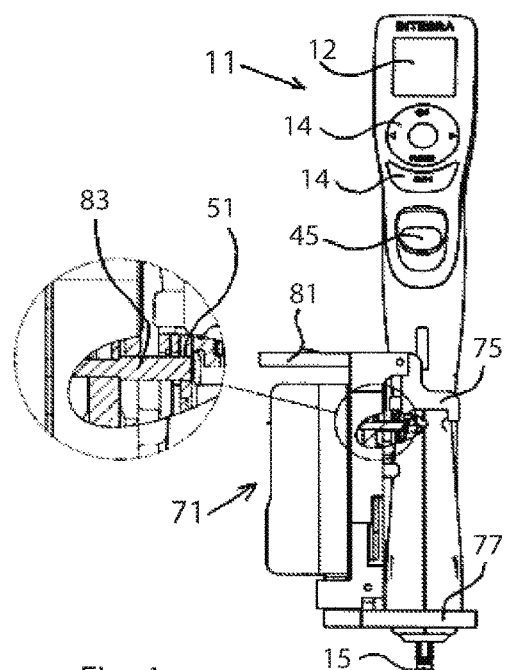
FIG. 4 a side view of the pipette and the device from FIG. 2 in the connected state.

The device 71 shown in FIGS. 2, 3, and 4 comprises a movable part in the shape of a pin 83 as well as a holder 73 for holding the pipette 11.

The second operating element 47 has an opening 51, in which the pin 83 is incorporated, when placing the pipette 11 in the holder 73. The pin 83 is movable by means of a drive, whereby the movement of the second operating element 47 (and thereby the operating of the ejection mechanism) is caused due to the inclusion of the pin 83 in the opening 51 by the movement of the pin.

The holder in the shown example possesses two lower brackets 77, which support the pipette 11 and counteract movement due to the pin 83 when activating the ejection mechanism. The holder additionally has two top brackets 75 that counteract movement of the pipette 11 in the other (opposing) movement direction of the pin 83. The top brackets 75 are rotatable upwards by operating a lever 81 and/or away from the bottom brackets 77, which allows for an inclusion and removal of the pipette 11 in the holder 73 or out of the holder. But the holder 73 can naturally also be designed in a different manner.

It is preferred that the pipette 11 controls the device 71. For this purpose, the pipette 11 may comprise a memory that contains information. The information may be entered by the user via input elements (e.g. in the form of buttons 14) and/or display 12 as described above. The pipette 11 and the device 71 each comprise a communication device to transmit the information from the pipette 11 to the device. Accordingly, the pipette 11 is designed and/or programmed for the transmission of the information to the device 73, and the device 73 to receive the information from the pipette, whereby the device 73 is controlled depending on the information. The drive described above, which serves the operating of the second operating element 47, can especially be controlled depending on the information.

However, the device 71 may also be part of a positioning device to position the pipette. Such a positioning device may comprise one, two, or more other holders to hold containers, whereby the holder 73 for the pipette may be formed movable relative to one or more of the other holders, so that the pipette can be moved from a first to a second container, for example, by means of the positioning device. In order to perform the movement of the holder 73 for the pipette relative to one or relative to the several other holders, the positioning device may comprise one or more other drives. Provision may be made that this (these) movement(s) is also done depending on the said information and/or if the positioning device is designed and/or programmed to execute the said movement(s) depending on the information.

The device 71 is not necessary for the intended use of the pipette 11. The latter is merely an additional device. The ejection mechanism is especially also operable without the device 71 (by means of the first operating element) and/or the ejection mechanism is part of the pipette. By using the device 71, the removal of the pipette tips is however facilitated. It is particularly useful when using the device 71 as a positioning device.

LIST OF REFERENCE SIGNS

11 Pipette
12 Display
13 Handle
14 Buttons
15 Interconnecting part
21 Housing
23 Opening
43 Slider
45 first operating element
47 second operating element
49 movable member
51 Opening
71 Device for operating the ejection mechanism
73 Holder
75 top brackets
77 bottom brackets
81 Lever
83 Pin

What is claimed is:
1. A handheld pipette comprising:
A handle;
An interconnecting part to attach a pipette tip;

An ejection mechanism to remove the pipette tip from the interconnecting part, wherein the ejection mechanism comprises a movable slider being arranged on the interconnecting part and is movable relative to the interconnecting part in the area of the interconnecting part that is adapted to remove the pipette tip from the interconnecting part when operating the ejection mechanism, and Further wherein the pipette comprises a first and second operating element each mechanically coupled to the ejection mechanism and each accessible from the outside to operate the ejection mechanism, The first operating element being arranged in the area of the handle and operable by hand, and The second operating element adapted to be mechanically operated from outside of the pipette to operate the ejection mechanism and move the slider to remove a pipette tip from the interconnecting part; and The pipette further comprises a housing below the area of the handle, whereby the second operating element is located within the housing and is configured to be accessible from the outside through an opening in the housing.

2. The pipette according to claim 1 wherein the second operating element is configured to interact with a movable part of an external device in order to operate the ejection mechanism.

3. The pipette according to claim 2 wherein the pipette is an electronic pipette, and further wherein the pipette comprises a memory, whereby the memory contains information to control the external device for activating the ejection mechanism, and whereby the pipette comprises a communication device to transmit the information to the external device for activating the ejection mechanism.

4. The pipette according to claim 1 wherein the slider is adapted to contact the pipette tip and slide the pipette tip from the interconnecting part when operating the ejection mechanism, whereby the slider is movable relative to the interconnecting part along a longitudinal axis of the interconnecting part and along a longitudinal axis of the pipette tip attached on the interconnecting part.

5. The pipette according to claim 1 wherein the ejection mechanism is adapted to transfer force exerted from a user onto the first operating element to the slider, whereby the ejection mechanism comprises a movable member relative to the interconnecting part connected with the slider for this purpose, so that movement of the first operating element effects a movement of the movable member.

6. The pipette according to claim 1 wherein the opening in the housing is closable by a movable closure arranged on the housing.

7. The pipette according to claim 1 wherein the pipette is a multi-channel pipette that comprises several interconnecting parts to attach one pipette tip each.

8. A system comprising:
A handheld pipette comprising:
A handle;
An interconnecting part to attach a pipette tip;
An ejection mechanism to remove the pipette tip from the interconnecting part, wherein the ejection mechanism comprises a movable slider being arranged on the interconnecting part and is movable relative to the interconnecting part in the area of the interconnecting part that is adapted to remove the pipette tip from the interconnecting part when operating the ejection mechanism, and Further wherein the pipette comprises a first and second operating element each mechanically coupled to the ejection mechanism and each accessible from the outside to operate the ejection mechanism, The first operating element being arranged in the area of the handle and operable by hand, and The second operating element adapted to be mechanically operated from outside of the pipette to operate the ejection mechanism and move the slider to remove a pipette tip from the interconnecting part; wherein The pipette further comprises a housing below the area of the handle, whereby the second operating element is located within the housing and is configured to be accessible from the outside through an opening in the housing; and An external device to operate the ejection mechanism of the pipette wherein the external device comprises a drive and a movable part that is moved by the drive, whereby the movable part is adapted to interact with the second operating element of the pipette to operate the ejection mechanism.

9. The system according to claim 8 wherein the external device comprises a holder to hold the pipette, and the drive and the movable part are positioned relative to the holder in such a way that when the second operating element is in the connected state, when the pipette is held in the holder, the ejection mechanism is operable through the movable part on the external device.

10. The system according to claim 9 wherein the external device is adapted to receive information from the pipette and to operate the second operating element depending on this information, whereby the external device comprises a communication device to receive the information and a microprocessor to process the information and to control the drive for this purpose.

11. The system according to claim 10 wherein the external device is a positioning device to position the pipette during the collecting and dispensing of samples from or to a first container or a second container, whereby the external device in addition to the first holder recited in claim 10 further comprises a second holder to hold the first or second container and a second drive to move the first holder relative to the second holder, and further whereby the external device is adapted to perform the positioning of the pipette depending on the information and execute the movement of the first holder relative to the second holder.

12. A procedure for removing a pipette tip from the interconnecting part of a handheld pipette with a handle, said pipette comprising an ejection mechanism to remove the pipette tip from the interconnecting part as well as a first and a second operating element to operate the ejection mechanism, said first operating element being arranged in the area of the handle and operable by hand, said procedure comprising the steps of:
bringing the pipette into contact with an external device for operating the ejection mechanism;
engaging the second operating element with a movable part of the external device; and
operating the external device to move the movable part and operate the second operating element of the ejection mechanism.

13. The procedure according to claim 12 wherein the external device comprises a holder and the pipette is held in the holder, whereby the movable part of the external device when the pipette is held in the holder is engaged with the second operating element, and further wherein the pipette is an electronic pipette with a memory containing information to control the external device for operating the ejection mechanism, the pipette and the external device comprise a communication device each, and the information is thereby transmitted from the pipette to the external device, and the external device comprises a drive to move the movable part.

* * * * *